(12) United States Patent
Calciolari et al.

(10) Patent No.: US 8,664,965 B2
(45) Date of Patent: Mar. 4, 2014

(54) DEVICE FOR THE MEASUREMENT OF ELECTRICAL PROPERTIES OF FLUIDS AND METHOD FOR MEASURING SAID ELECTRICAL PROPERTIES

(75) Inventors: Paolo Calciolari, Lonigo (IT); Stefano Bernardi, Padua (IT)

(73) Assignee: Pietro Fiorentini SpA, Arcugnano (VI) (IT)

( * ) Notice: Subject to any disclaimer, the term of this patent is extended or adjusted under 35 U.S.C. 154(b) by 0 days.

(21) Appl. No.: 12/997,928

(22) PCT Filed: Jul. 20, 2010

(86) PCT No.: PCT/EP2010/004428
§ 371 (c)(1),
(2), (4) Date: Jan. 13, 2011

(87) PCT Pub. No.: WO2010/145851
PCT Pub. Date: Dec. 23, 2010

(65) Prior Publication Data
US 2012/0182030 A1 Jul. 19, 2012

(30) Foreign Application Priority Data
Jul. 21, 2009 (IT) .............................. VI2009A0183

(51) Int. Cl.
*G06F 3/041* (2006.01)
*G06F 3/042* (2006.01)

(52) U.S. Cl.
USPC ............................ 324/693; 345/173; 345/176

(58) Field of Classification Search
USPC .................................... 324/693; 345/173–178
See application file for complete search history.

(56) References Cited

U.S. PATENT DOCUMENTS

| | | | |
|---|---|---|---|
| 4,975,645 A * | 12/1990 | Lucas | 324/324 |
| 5,134,380 A | 7/1992 | Jonas | |
| 5,216,409 A | 6/1993 | Ament et al. | |
| 5,736,637 A * | 4/1998 | Evans et al. | 73/152.31 |
| 7,138,806 B2 * | 11/2006 | Gafner et al. | 324/660 |
| 2006/0290363 A1 * | 12/2006 | Botelho | 324/754 |

FOREIGN PATENT DOCUMENTS

CH 326215 A 12/1957
EP 1411348 A1 4/2004

* cited by examiner

*Primary Examiner* — Jermele M Hollington
*Assistant Examiner* — Farhana Hoque
(74) *Attorney, Agent, or Firm* — IP Strategies

(57) ABSTRACT

Device (2) for measuring electric parameters of a fluid (F), comprising: two measurement circuits (8, 10) for measuring, respectively, the dielectric permittivity and the electrical conductivity of the fluid (F); two electrodes (5, 5') facing each other from opposite sides of the fluid (F); a selector system (11) for alternatively connecting the two measurement circuits (8, 10) to the electrodes (5, 5'). Each electrode (5, 5') comprises two sectors (5a, 5b) suited to establish mutually separate electrical contact with the fluid (F) and the electrical conductivity measurement circuit (10) comprises two measurement sections (V, A) of different impedance, each one of which being connectable to a corresponding sector (5a, 5b) of each electrode (5, 5').

4 Claims, 8 Drawing Sheets

DEVICE FOR THE MEASUREMENT OF ELECTRICAL PROPERTIES OF FLUIDS AND METHOD FOR MEASURING SAID ELECTRICAL PROPERTIES

FIELD OF THE INVENTION

The present invention regards a device for measuring the properties of dielectric permittivity and electrical conductivity of a fluid.

The aforesaid device is particularly suitable for use in an apparatus for measuring the concentration and the flow rate of the different fractions or phases constituting a non-homogeneous fluid.

The present invention also regards a method for executing the aforesaid measurement.

BACKGROUND OF THE INVENTION

As is known, the aforementioned type of apparatuses and methods are widely used in the oil production sector.

In fact, the fluids extracted from oil wells are non-homogeneous mixtures of oil, salt water and gas, known in the sectors jargon as "multiphase fluids".

To determine the amount of extracted oil and, in particular, the profitability of the well, it is necessary to determine with precision not only its flow rate, but also the concentration of the different phases composing the fluid.

It is known that the aforesaid parameters are determined using the so-called "multiphase" apparatuses, which include a plurality of sensors adapted to measure various properties of the fluid including, for example, the differential pressure, the density and various electrical properties.

Combining the results of the aforesaid measurements by means of correlation models and known "cross-correlation" algorithms, it is possible to calculate the concentrations and the flow rate of the different phases of the fluid.

One of the most commonly measured quantities is the dielectric permittivity, which varies as a function of the percentages of the different phases in the mixture and, therefore, is a very useful input for the determination of their respective concentrations.

As it is well known to the man skilled in the field, this measure only allows the attainment of reliable results when the oil is the continuous phase in the liquid, which normally occurs when the fraction of oil is relatively high with respect of that of water.

However, it is also known that during extraction the percentages of the different phases in the fluid, in particular the fraction of gas, are not constant but are subject to quick fluctuations.

The fraction of water also tends to gradually increase with time, according to well's exploitation.

It follows that the dielectric permittivity alone is not sufficient for a precise measurement of the concentration of the mixture moment by moment.

When the fraction of water increases, the liquid phase eventually change to a water continuous flow and the liquid becomes conductive.

The permittivity reading will in this case have to be replaced by a conductivity reading for the determination of the concentration of the different components.

In fact, the water present in the mixtures extracted from oil wells is salt water and, therefore, its electrical conductivity exceeds that of oil by several orders of magnitude.

In order to determine the precise concentration of the mixture independently of the fraction of water it contains, the known techniques make use of an electrical conductivity sensor combined with a capacitance sensor for measuring the dielectric permittivity.

In particular, one of these known techniques, disclosed in document U.S. Pat. No. 5,736,637, uses two pairs of electrodes immersed in the fluid.

The first electrode pair is in electrical contact with the fluid, so as to have a low impedance that makes it suitable to measure the conductivity of the fluid.

The second pair of electrodes is electrically insulated from the fluid and, therefore, has a high impedance and is suitable for measuring the dielectric permittivity of the fluid.

Each pair of electrodes is connected to a corresponding measurement circuit which is optimised for giving the measure of the respective electric quantity with a predetermined precision within the common range of variation of that electrical quantity.

The two pairs of electrodes are placed close to each other, so that the two electric quantities are measured in sections of the fluid very close to each other.

In order to avoid interference between the two pairs of electrodes, which would cause significant measurement errors, the circuits are activated alternatingly to each other, so that, when one circuit is active, the pair of electrodes corresponding to the other circuit is insulated.

The two measurements are executed almost simultaneously, using electronic switches which ensure high commutation frequency.

However, due to the presence of two pairs of electrodes, the aforesaid known technique poses the drawback that the sensor is particularly bulky.

The aforesaid drawback is particularly disadvantageous in the field of oil wells, where the available space is reduced and the sizes must be minimised.

The same drawback is even more evident when several electrodes are used in combination, in order to being able to use cross-correlation algorithms to determine the speed of the fluid.

The presence of two pairs of electrodes implies the further drawback of doubling the number of connections between the electrodes and their respective measurement circuits, causing the device to be more complicated and the risk of failures to increase.

In some subsea installations where the requirements for redundancy is high sometimes three or even four sensors are used, which further worsen the above mentioned drawbacks.

In addition, although the two pairs of electrodes are close to each other, the respective measurements are executed in two different zones of the pipe which, due to the erratic composition of the mixture, generally contain quantities of fluid having different composition.

Consequently the correlation of the two measurements, necessary to establish the global electrical properties of the fluid from moment to moment, introduces errors that limit the precision of the measurement.

In the attempt to overcome the aforesaid drawbacks, another known device makes use of three electrodes rather than four, two of which are transmitter electrodes while the third acts as a common receiver electrode and is kept virtually earthed.

One of the two transmitters is in electrical contact with the fluid while the second is insulated with respect to it.

This way, the first electrode has a lower output impedance with respect to the second electrode, so that the two electrodes coupled with the receiver can measure the electrical conductivity and the dielectric permittivity of the fluid, respectively.

The two transmitters are fed with different signals, for example in quadrature phase or with different frequencies, so that it is possible to separate the signals coming from each transmitter to allow determination of permittivity and conductivity values.

This device has a lower number of electrodes than the preceding device but, nonetheless, it requires the use of a specific transmitter electrode for each electric quantity, thus being partially subject to the aforementioned drawbacks.

In addition, both the aforesaid known devices pose the drawback of not allowing a precise measurement of the electrical conductivity of the fluid.

In fact, the measured resistance between the electrodes also includes the impedance at the interface between the electrodes and the fluid, called "transfer impedance" in the technical jargon, which is not known beforehand and, therefore, causes measurement errors.

Another disadvantage of both known devices described above lies in that they are subject to an error in the permittivity measurement.

In fact, the electrodes used to measure the conductivity introduce a stray capacitance that could, in some cases, affect the permittivity measurement.

Document U.S. Pat. No. 5,216,409 further discloses a device for detecting contaminants in an alcohol-gasoline mixture for internal combustion engines. This device uses a single sensor, which is switched between different circuitry for measuring both permittivity and conductivity.

Document CH 326 215 discloses an apparatus for displaying the properties of softening solutions of water treatment plants by measuring the conductivity of the solution through an electrode pair.

BRIEF SUMMARY OF THE INVENTION

The present invention is intended to overcome all the aforementioned drawbacks that are typical of the prior art.

In particular, the first object of the invention is to provide a measuring device for the dielectric permittivity and electrical conductivity of a fluid that is more compact than the known devices described above.

Another object of the invention is to provide a measuring device and method allowing a more precise identification of the fluid compared to that permitted by the prior art.

The aforesaid objects are achieved by a measuring device constructed as specified in claim 1.

The aforesaid objects are also achieved by a measurement method implemented according to claim 10.

In particular, the invention comprises the use of an electrical conductivity measurement circuit, a dielectric permittivity measurement circuit and a selector system to connect the aforesaid circuits alternatingly to the same pair of electrodes in electrical contact with the fluid.

The aforesaid configuration allows the number of electrodes to be halved compared to known devices based on two pairs of electrodes, favourably reducing the size of the device while at the same time providing equal measurement precision.

Advantageously, the greater compactness of the device that is the subject of the invention compared to the known devices just mentioned facilitates its installation in oil wells, where the available space is limited.

This is particularly advantageous in the calculation of the fluid speed by means of cross-correlation algorithms, which require to combine a minimum of two pairs of sensors measuring the same electrical property.

Another advantage lies in that the device of the invention has a smaller number of electrical connections between the electrodes and the measurement circuits connected to them, because a single connection is needed between each electrode and the selector system.

Consequently and advantageously, the device of the invention is less subjected to the risk of breakdowns compared to the devices of known type.

In addition, since the device of the invention has only two electrodes, the permittivity measurement is not affected by errors generated by stray capacitance induced by the presence of other electrodes in the surroundings. Still advantageously, being that both measurements of electrical conductivity and dielectric permittivity are carried out in the same portion of the fluid, a sufficiently fast switching between them makes it possible to define with greater precision the instantaneous concentrations of the different fractions of fluid, despite their fluctuations.

Advantageously, said greater precision of the device of the invention compared to the known devices enables a more accurate evaluation of the profitability of the well.

The invention further provides that each electrode be divided into two sectors, each of which is suited to establish an electrical contact with the fluid separately from the other sector.

For the electrical conductivity measurement, the two sectors of each electrode can be used to carry out two separate measurements, so as to allow implementing a measuring technique known in electronics as the "four-wire method", which advantageously allows higher measurement precision compared to equivalent known devices based on the two-wire method.

BRIEF DESCRIPTION OF THE DRAWINGS

The aforesaid objects and advantages, together with those better described below, will be understood on the basis of the description of some preferred embodiments of the invention, with reference to the attached drawings, which are provided merely for illustrative purposes and in no way exhaustive and/or limiting, wherein.

DETAILED DESCRIPTION OF THE INVENTION

Figure 1:
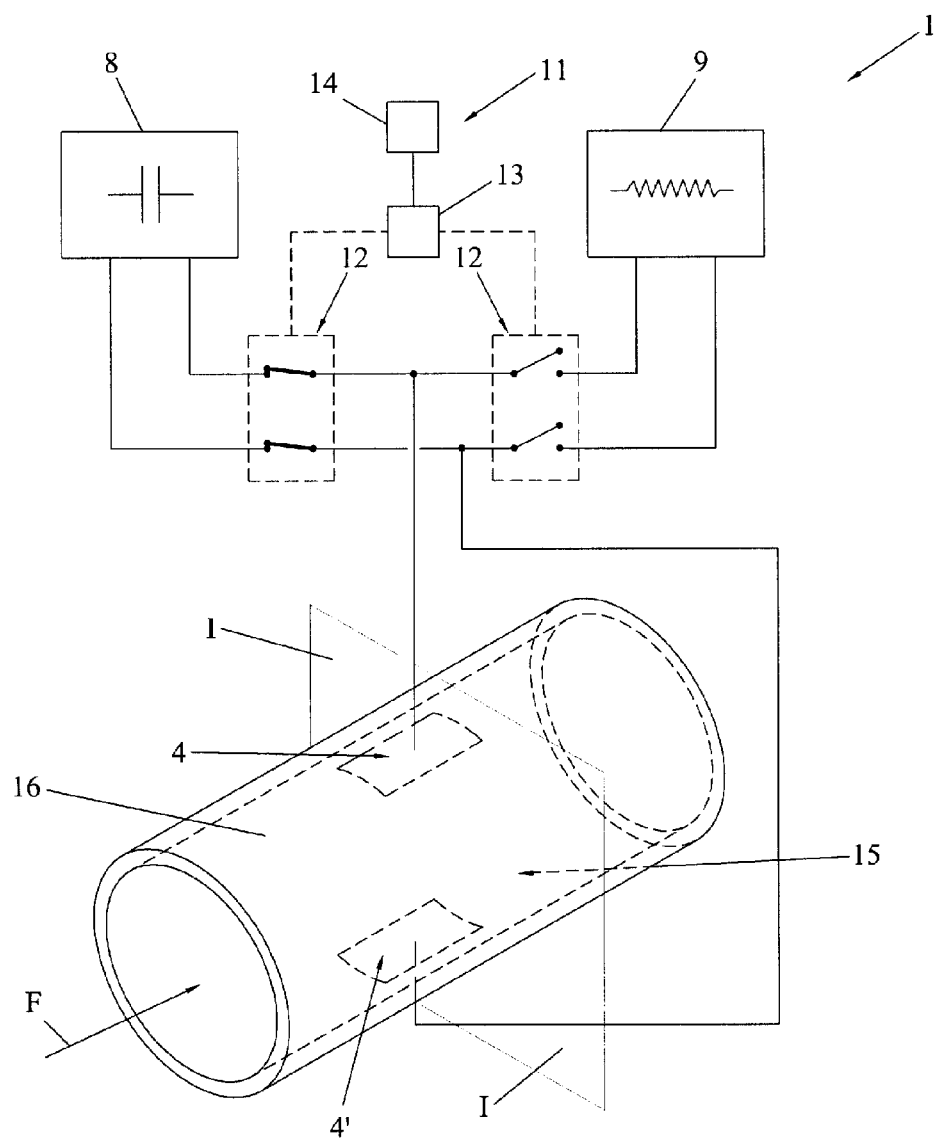
FIG. 1 shows a diagram of a measuring device according to the prior art.

A device of known type, suitable for the measurement of the dielectric permittivity and electrical conductivity of a fluid, is schematically represented in FIG. 1, where it is indicated as a whole by number 1.

The device 1 is particularly suitable for determining the concentrations of the different phases of a multiphase mixture F having at least two phases with different impedance, in particular of a non-homogeneous mixture extracted from an oil well.

The device 1 includes a dielectric permittivity measurement circuit 8 and an electrical conductivity measurement circuit 9.

For greater clarity, the dielectric permittivity measurement circuit 8 is indicated in the figures with the symbol of a capacitor, while the electrical conductivity measurement circuit 9 is indicated with the symbol of a resistance.

Each measurement circuit 8, 9 is able to measure the corresponding electric quantity of the fluid F between a pair of electrodes placed in electrical contact with the fluid itself.

Advantageously, the availability of two different measurement circuits, one for each electric quantity, allows to optimise each of them to obtain the maximum measurement sensitivity, considering that the ranges of the values of both quantities differ by several orders of magnitude.

In addition, the device 1 includes two electrodes 4, 4', whose material is suitable for establishing an electrical contact with the fluid F, and is preferably steel or any other metal or alloy able to resist the aggressive action of salt water and other substances present in the fluid F.

The two electrodes 4, 4' face each other from opposite sides of a containment volume 15 for the fluid F that, preferably but not necessarily, is defined by the walls of the pipe 16 in which the fluid flows.

Figure 1A:
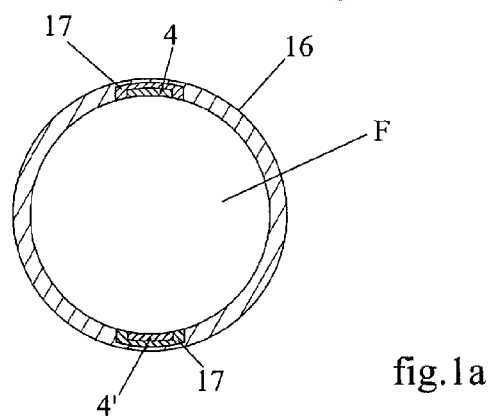
FIG. 1a shows the pipe in which the device shown in FIG. 1 is inserted, in cross sectional view according to plane I-I.

As can be seen in FIG. 1a, the electrodes 4, 4' are installed preferably on the internal wall of the aforesaid pipe 16 and embedded in the wall itself, so as to maintain the continuity of the surface.

Preferably, the two electrodes 4, 4' are diametrically opposed with respect to each other.

Since the different fractions of a multiphase fluid are not homogeneously distributed in the pipe section, due to their different density, the above described position of the electrodes allows advantageously to measure the average properties of the fluid F through the entire section of the pipe 16.

However it is clear that, in different embodiments of the device 1 not represented herein, the electrodes 4, 4' can be installed in any way, provided that they allow the measurement of the properties of the fluid F between the electrodes themselves.

The device 1 has a selector system 11 able to connect each one of the two measurement circuits 8 and 9 to the electrodes 4, 4' alternatingly to the other circuit, in order to measure the respective electrical quantity in the volume of fluid 15 included between the electrodes.

It can be understood that the aforesaid selector system 11 allows the measurement of both the dielectric permittivity and the electrical conductivity of the fluid F to be carried out using a single pair of electrodes 4, 4', by connecting each of the two measurement circuits 8, 9 to the electrodes in order to obtain the aforesaid measures separately from each other.

Consequently, the device 1 described above has a smaller number of electrodes and, therefore, is more compact, with respect to other equivalent known devices.

Still advantageously, the selector system 11 allows reduction of the number of connections between the measurement circuits 8, 9 and the electrodes 4, 4'.

In fact, as can be seen in FIG. 1, there is a single connection line leaving from each electrode 4, 4' which bifurcates only close to the measurement circuits 8, 9, at the level of the selector system 11.

Preferably, the aforesaid selector system 11 includes switches 12 interposed between each measurement circuit 8, 9 and each electrode 4, 4', interconnected by a synchronising unit 13 which coordinates their activation.

For the sake of clarity, the Figures show the closed switches in thick line.

FIG. 1 shows the device with the aforesaid switches 12 in a configuration where the electrodes 4, 4' are connected to the permittivity measurement circuit 8, as a non-limiting example.

Clearly, the electrodes 4, 4' can also be connected to the conductivity measurement circuit 9, by changing the positions of the switches 12 with respect to the ones represented in FIG. 1.

It is clear that the presence of an electronic switch 12 in each connection line allows the complete separation of each measurement circuit 8, 9 from both electrodes 4, 4'.

The aforesaid separation between the two measurement circuits allows, advantageously, to configure them independently of each other, so as to optimise each of them based on the range of variations of the corresponding quantity to be measured.

Anyway it is obvious that, in other embodiments of the device, one of the electrodes of the pair 4, 4' can be left permanently connected to the measurement circuits 8 and 9 and the switching can only occur on the other electrode of the pair, provided that a suitable electronic system is available to manage the large impedance difference between the two measurements.

Preferably, the switches 12 are electronic switches that, advantageously, allow a much faster switch-over between each measurement circuit 8, 9 and each of the connection lines to the electrodes 4, 4'.

The aforesaid high switching speed allows the execution of any predefined sequence of multiple permittivity and conductivity measurements substantially at the same time.

Consequently it is possible, for example, to determine which one of the two conductive or permittive states prevails in the fluid in a predefined moment, so as to choose the most significant measure based on the instantaneous concentration of the fluid.

In addition, advantageously, since both the measurements are related to the same fluid portion, it is possible to calculate the instantaneous concentration of the fluid in a more reliable way compared to the known techniques.

Preferably, the aforesaid switch-over sequence between the two measurement circuits 8, 9 is synchronised by means of a management unit 14 connected to the selector system 11.

As regards the electrodes 4, 4' shown in FIG. 1, each of them is constituted by a single conductive plate.

Figure 2:
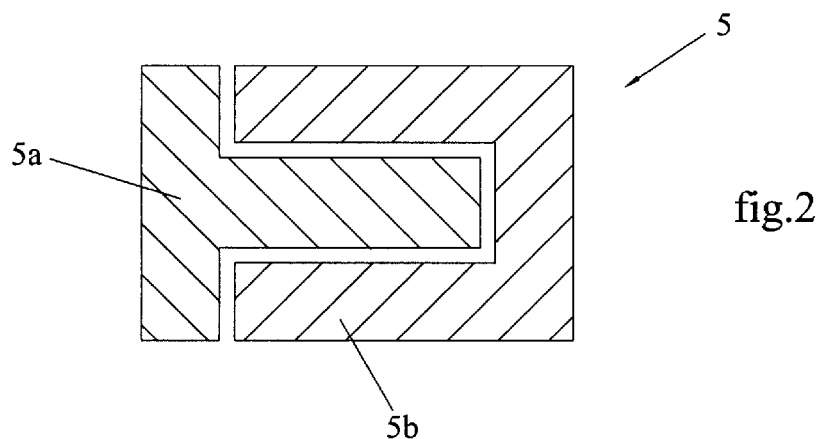
FIG. 2 shows a component of the device that is the subject of the invention.
Figure 5A:
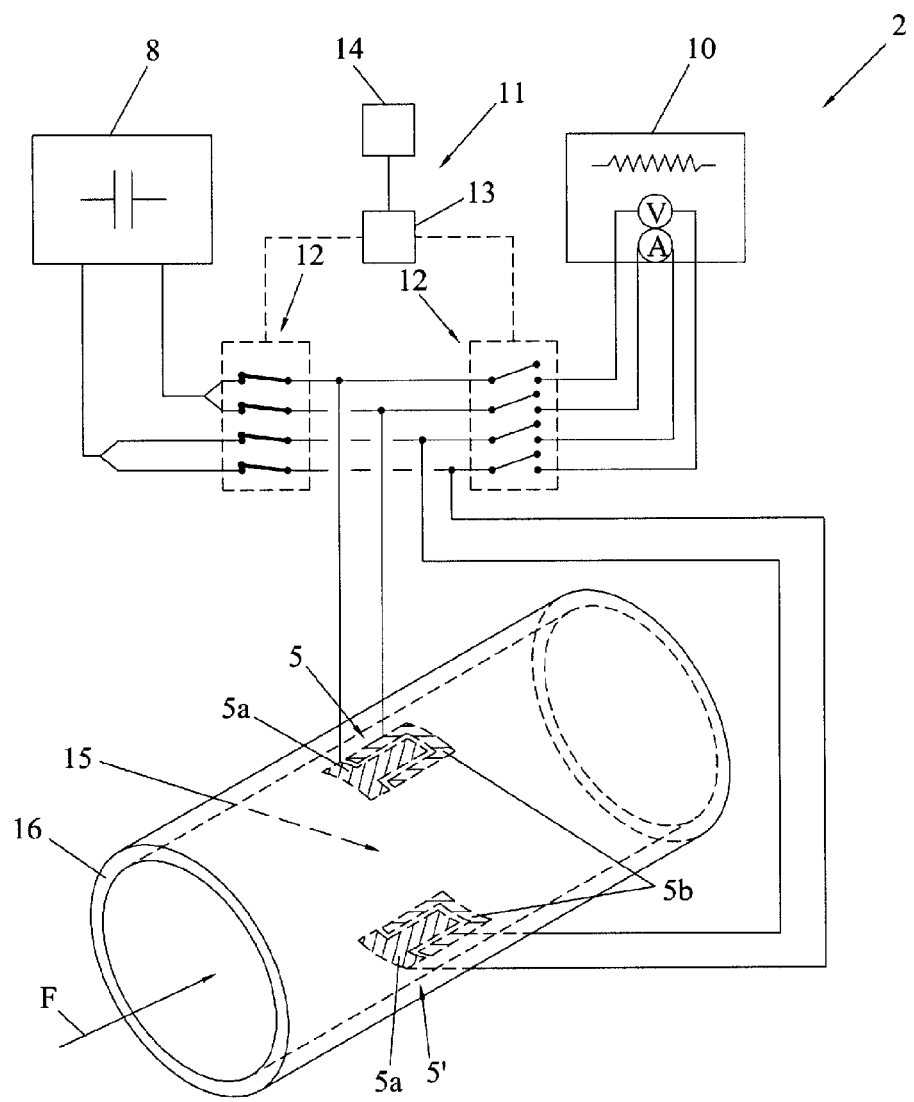
FIGS. 5a and 5b show an embodiment of the device that is the subject of the invention, in two different operating phases.

FIG. 5a represents the device 2 according to the invention, which includes two electrodes 5, 5' different from the preceding ones, shown in detail in FIG. 2.

In particular, each electrode 5, 5' is divided into two sectors 5a and 5b, each of which is suited to establish an electrical contact with the fluid F separately from the other sector.

More precisely, the two sectors 5a, 5b are separated from each other by any known insulating material, whose thickness should be such to ensure adequate electrical insulation and mechanical strength.

Preferably, for the dielectric permittivity measurement, each of the electrodes 5, 5' is used with the respective sectors 5a and 6b interconnected so as to behave as a whole, according to the schematic illustration in FIG. 5a.

Figure 5B:
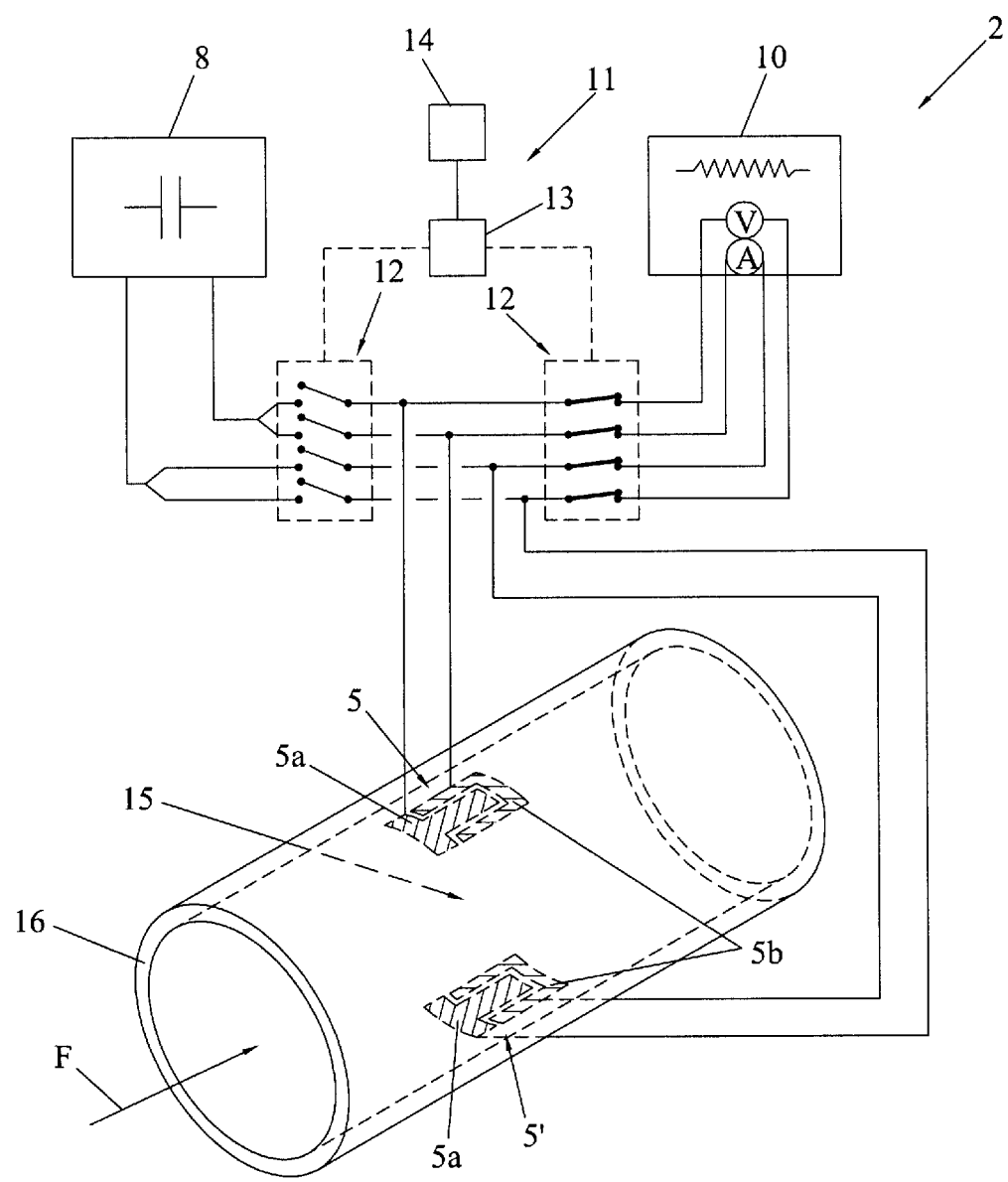

Vice versa, for the electrical conductivity measurement, schematically shown in FIG. 5b, the two sectors 5a, 5b of each electrode 5, 5' are used preferably to carry out two separate measurements, so as to advantageously allow the use of a measuring technique known in electronics as the "four-wire method".

As it is known, the four-wire method substantially consists in the measurement of the resistance of a resistor using a low impedance instrument (ammeter) to inject a current through the resistor and a high impedance instrument (voltmeter) to measure the voltage generated by the aforesaid current at both ends of the resistor, connected in parallel to the first and independent of it. Once the current and the voltage have been measured, Ohm's law permits the calculation of the resistance and, therefore, of the electrical conductivity of the resistor.

The advantage of the four-wire method lies in that the resistance of the connection wires between the voltmeter and the resistor does not substantially affect the instrument's indication, because of the high impedance of the voltmeter.

Consequently, the measured voltage at both ends of the resistor coincides in practical terms with that of both ends of the voltmeter.

The four-wire method is relevant to the device 2 of the invention because, as it is well known, a transfer impedance occurs between an electrode and a fluid when in contact, due to a resistance at the interface between the electrode and the fluid, and also to layers of oil, wax or other substances which can cover the electrode during operation.

The above mentioned transfer impedance is equivalent to the above mentioned resistance of the connection wires and, since it is unknown, it normally generates a measurement error.

This measurement error can be rendered negligible by using the above described four-wire method, as follows.

The conductivity measurement circuit 10 of the device 2 of the invention has two different measurement sections, of which a section A with low impedance acts as the ammeter and a section V with high impedance acts as the voltmeter.

Section A with low impedance is connectable for example to sector 5b of each electrode 5, 5' and is used to inject a primary current through the fluid F, while section V with high impedance is connectable to the other sector 5a of each electrode.

Of course, the above connections could also be inverted, since, for the end result, it does not matter which of the two sectors 5a, 5b is connected to section A and which to section V.

To measure the electrical conductivity of the fluid F, the section A with low impedance injects the aforesaid primary current between the corresponding sectors 5b of the two electrodes 5, 5', which generates a primary voltage through the fluid.

At the same time, section V with high impedance measures the voltage of the fluid between the other two sectors 5a of the electrodes 5, 5'.

Given the proximity between the two sectors 5a and 5b in each of the electrodes 5, 5', the voltage measured by the second section V is the primary voltage, excepting the voltage drop that occurs at the interface between the fluid F and each sector 5a of the electrodes connected to the second section V.

However, the high impedance of the second section V renders this voltage drop negligible with respect to the primary voltage.

Therefore, the voltage measured by the second section V is substantially equal to the primary voltage, advantageously allowing higher measurement precision compared to equivalent known devices based on the two-wire method.

Preferably, a sector 5a of each electrode 5, 5' is at least partially surrounded by the other sector 5b of the same electrode.

Advantageously, the aforesaid configuration favours the four-wire method precision for the measurement of electrical conductivity.

In fact, being the two sectors interpenetrated to each other, the portions of fluid between the two pairs of sectors mingle in a single portion, to which both the quantities measured by the two pairs of sectors refer.

FIG. 2 illustrates one of the multiple possible shapes of the electrode 5, which includes a T-shaped sector 5a and a U-shaped sector 5b, arranged around the central part of the first sector.

Figure 3:
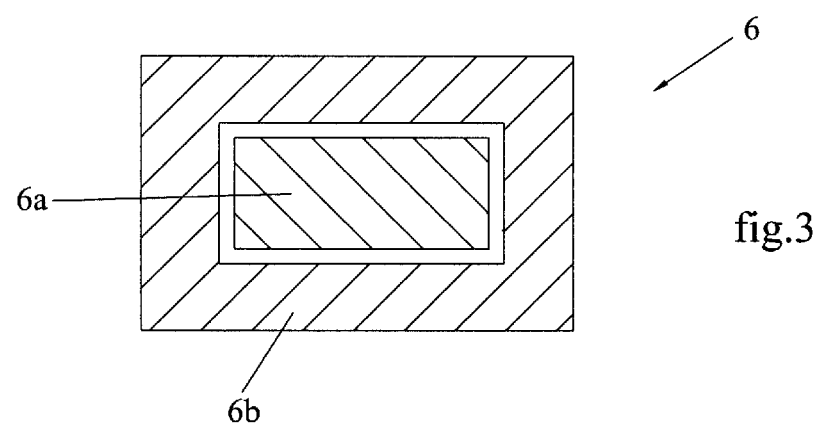
FIGS. 3 and 4 show further embodiments of the component shown in FIG. 2.

In the embodiment of the electrode indicated in FIG. 3 by numeral 6, a sector 6a is completely surrounded by the other sector 6b.

It is absolutely clear that, besides the embodiment shown in FIG. 3, many other can be implemented in which a sector at least partially surrounds the other, and all these embodiments are suitable to be used in the device of the invention, like the electrode in FIG. 2.

In any case, as already highlighted, for the purposes of measuring the electrical conductivity it is irrelevant which of the two sectors is used to inject current and which to measure the voltage.

In addition, while for reasons of symmetry it is preferable to pair two electrodes with the same shape, this does not exclude that different embodiments of the sensor can make use two distinct electrodes, each one of which is shaped according to the any one of the aforesaid embodiments.

In any case, independently of the shape of the electrodes comprised in each pair, the combination of two such pairs allows the use of known cross-correlation algorithms to determine the speed of the fluid.

Figure 4:
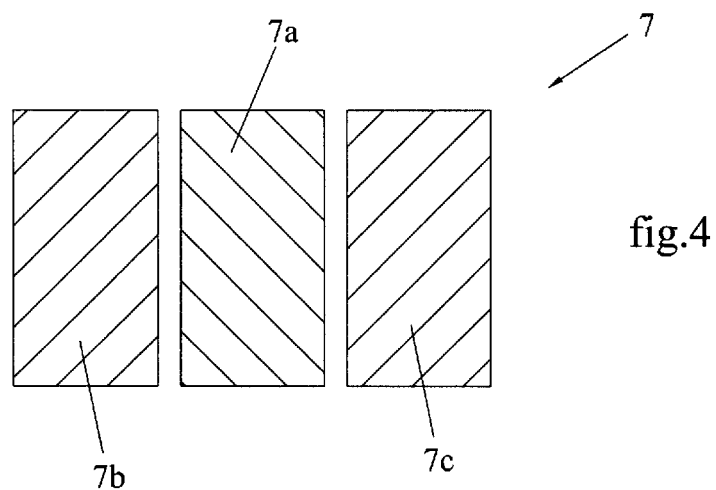

According to a further embodiment, shown in FIG. 4 and indicated as a whole by 7, the electrode comprises a first sector consisting of a single zone 7a of the electrode itself, and a second sector that is further divided in two separate zones, 7b and 7c.

Figure 6A:
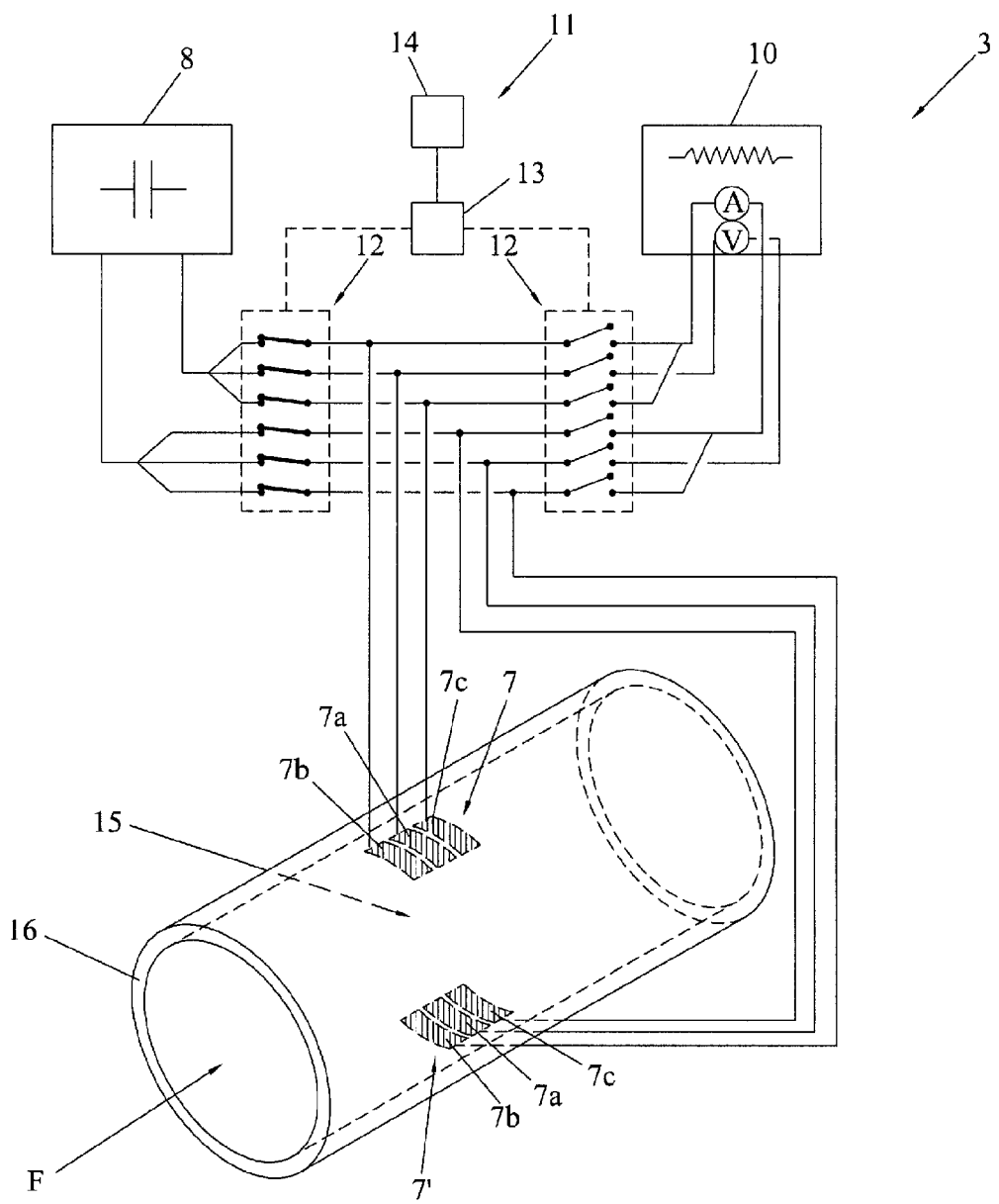
FIGS. 6a, 6b and 6c show a further embodiment of the device of the invention, in three different operating phases.

Each of the zones 7b and 7c is connectable to at least one of the measurement circuits 8 and 10 by means of independent electronic switches 12 and independently of the other zone, as shown in FIG. 6a, in which the device is indicated by number 3.

Two electrodes 7, 7' constructed according to this embodiment can be arranged to face each other as shown in FIG. 6a, so that each zone 7a, 7b and 7c of the electrode 7 and the corresponding zone 7a, 7b and 7c of the electrode 7' can be connected to one of the measurement circuits 8 or 10 independently of the other pairs of zones.

It is therefore possible to measure the permittivity or the conductivity of the portion of fluid between any one of the pairs of zones 7a-7a, 7b-7b and 7c-7c independently of the other zones.

Advantageously, the presence of three pairs of zones 7a-7a, 7b-7b and 7c-7c gives the electrode 7 greater reliability compared to the known electrodes inasmuch as, even in the case of malfunction of one pair, the four-wire measurement can in any case be executed using the two remaining pairs.

Preferably, the connections between the zones of the electrodes 7, 7' and the measurement circuits 8, 10 are established through electronic switches 12 connected to the aforesaid synchronising unit 13, in the same way described for the aforementioned embodiments.

Advantageously, the electronic switches 12 allow the attainment of the measurements between the three pairs of zones 7a-7a, 7b-7b and 7c-7c in rapid sequence, so as to process them with an already known cross-correlation algorithm to determine the speed of the fluid F.

Therefore, it is clear that this embodiment allows the determination of the speed of the fluid using a single pair of electrodes rather than two, with the advantage of less space needed for their installation compared to the known sensors.

Figure 6B:
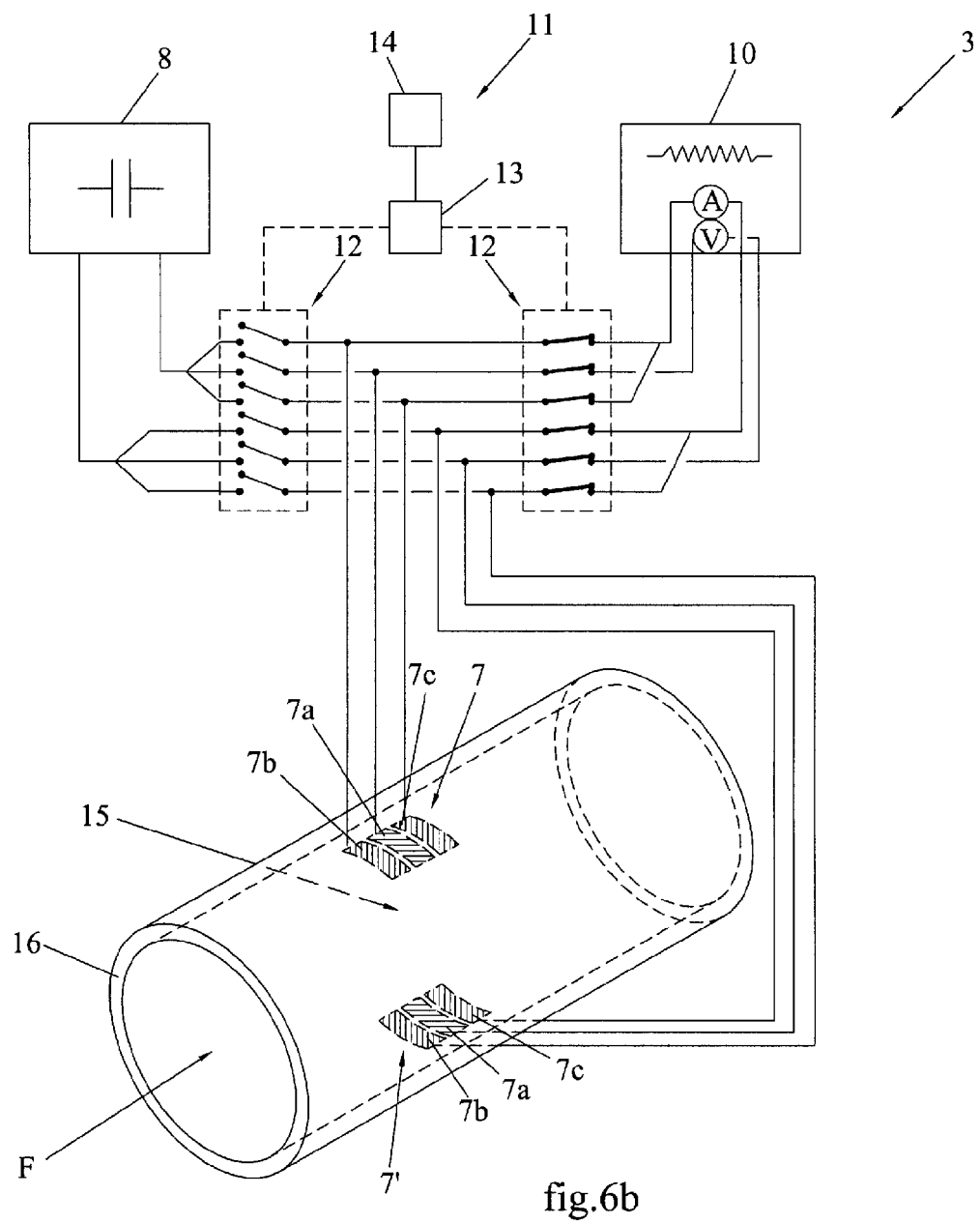
Figure 6C:
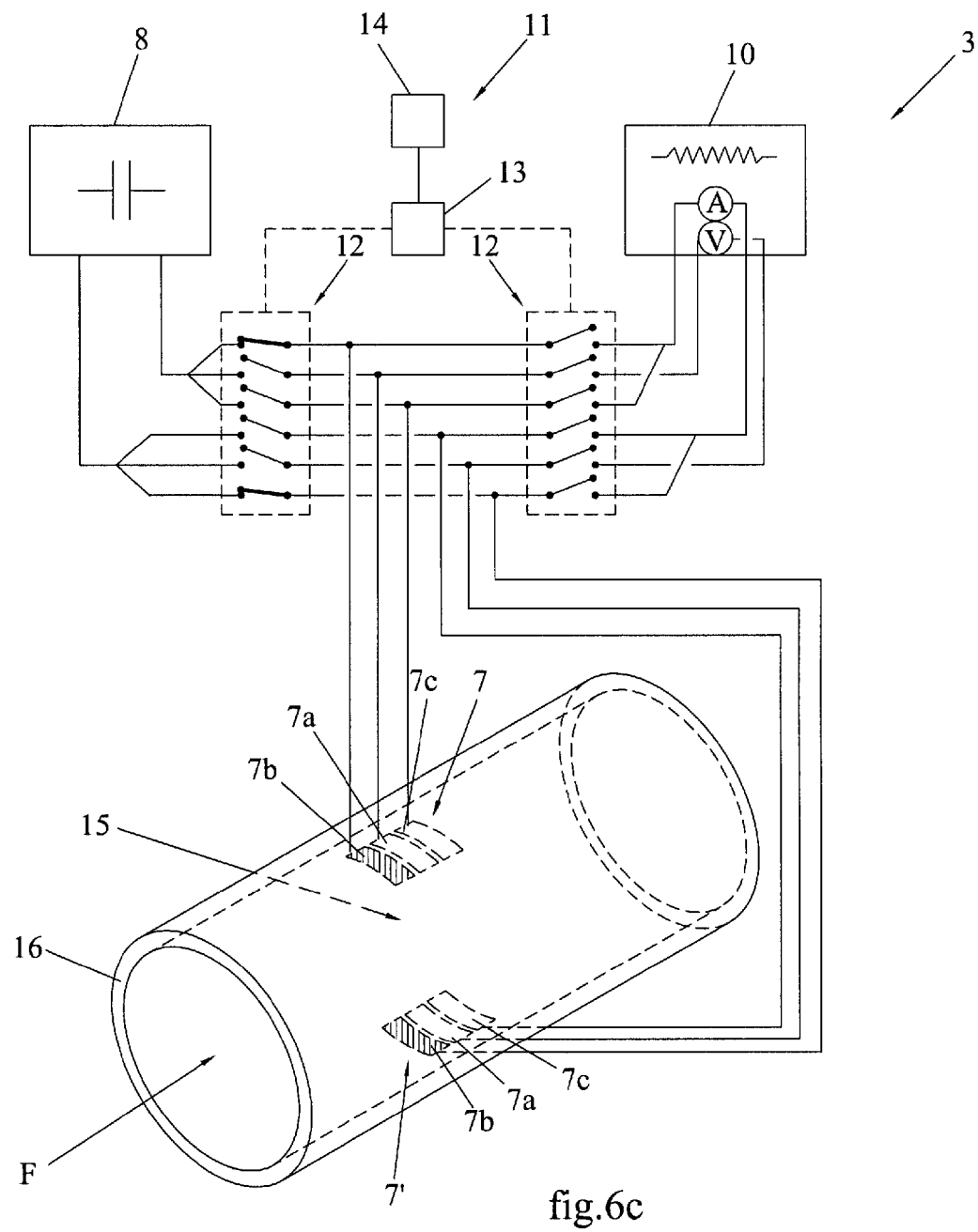

For illustrative purposes, FIG. 6c shows the positions of the switches 12 during the connection between the permittivity measurement circuit 8 and a pair of zones 7b-7b of the electrodes 7, 7'.

The connection between the conductivity measurement circuit 9 and the other pairs of zones, although not represented, occurs exactly in the same way, by closing the switches 12 associated with the corresponding zones and opening the others.

In different embodiments of the invention, the measures for the processing of the cross-correlation can be carried out only with two pairs of zones of the electrodes 7, 7' rather than with all three, preferably with the external, 7b and 7c, which are farther from each other.

The choice between two or three measurements is made as a compromise between the two opposite requirements of precision and constructive complexity required from the device 3.

According to a more complex embodiment of the invention, each pair of zones 7a-7a, 7b-7b and 7c-7c is selectively connectable to each of the measurement circuits 8 and 10, so as to apply the cross-correlation to the most representative electric quantity in relation to the concentration of the fluid in the various moments.

Preferably and as can be seen in FIG. 4, the two zones 7b, 7c belonging to the same sector are placed on opposite sides with respect to the first sector 7a, so that the latter is partially surrounded by the other sector, in such a way as to replicate what happens in the embodiments previously described.

It is clear that, in order to measure the dielectric permittivity and the electrical conductivity of the fluid using the third embodiment 7 of the device of the invention just described, the process is exactly the same as in the previously described embodiments 2, 3.

In particular, in the measurement of the dielectric permittivity each electrode is used with all of the respective zones 7a, 7b and 7c interconnected, as illustrated in FIG. 6a.

On the other hand, the measurement of the electrical conductivity is carried out with a sector 7a connected to one of the measurement sections, and with the two zones 7b, 7c of the other sector connected to each other and to the other measurement section.

For example, FIG. 6b illustrates the sector 7a being connected to measurement section V, and the two zones 7b and 7c of the other sector being connected to the measurement section A.

Evidently, it is irrelevant which of the two sectors is connected to one measurement section A, V, and the above described connections could well be switched.

Therefore, advantageously and as previously pointed out, the embodiment 7 allows the speed, the dielectric permittivity and the electrical conductivity of the fluid F to be measured using a single device 3.

Consequently and advantageously, the device 3 is more compact and constructively simpler than the known devices that perform the same functions, both from the mechanical and electronic point of view.

It is clear that the three zones 7a, 7b and 7c comprising each electrode 7 can be constructed with any shape, even different from that represented in the figures, maintaining in any case the functions described above.

Whatever the shape of the electrodes, they are associated with a support structure which, preferably but not necessarily, is the pipe 16 transporting the fluid F.

The aforesaid support structure 16 is the electric earthing of the system and defines its reference voltage.

Preferably, as can be seen in FIG. 1a, the electrodes 4, 4' are associated with the support structure 16 through respective insulating elements 17, in such a way that none of them is directly connected to earth.

It is clear that the aforesaid configuration is applicable to any type of electrode 4, 5, 6 and 7 among those previously described.

The aforesaid insulation allows the electrodes to be powered in such a way as to create a so-called "virtual ground" system, with the advantages that will be soon clarified.

As regards the power supply for the device, in the measurement of dielectric permittivity the electrodes are excited with variable voltage signals with a predefined shape.

Preferably a single square signal should be used, which can be easily generated by an electronic power supply device.

The preferred duration of the signal is a few microseconds, corresponding to a frequency range in the order of 1 MHz, which turns out to be the most suitable for the measurement of the dielectric permittivity of oil.

In addition, the permittivity measurement circuit is preferably adapted to maintain one of the electrodes in a virtual ground condition, as previously pointed out.

Advantageously, the aforesaid virtual ground system allows to perform a permittivity measurement which is unaffected by the capacitance to ground from the electrodes and the electrode wires, which can be up to 100 times higher than the capacitance to be measured.

Figure 5C:
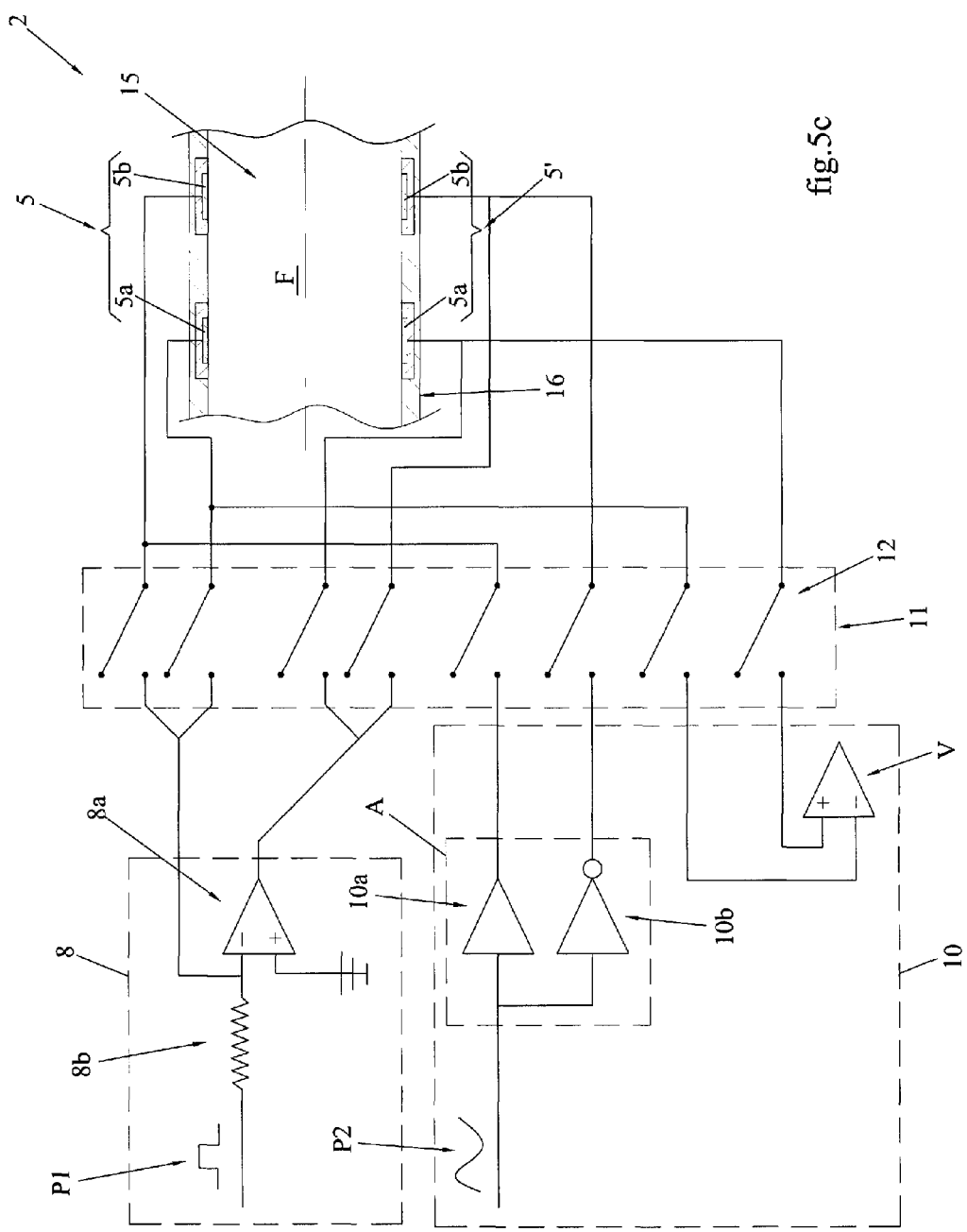
FIG. 5c shows a diagram of the device shown in FIGS. 5a and 5b.

FIG. 5c is a schematic representation of the circuit used to achieve the condition described above, relative to the embodiment of the device indicated by numeral 2.

Clearly the aforesaid circuit is applicable to any equivalent embodiment of the electrode.

During the measurement of permittivity, the switches 12 connected to the permittivity measurement circuit 8 are in closed state.

Therefore, the two sectors 5a and 5b of the electrode 5 are both connected to the negative input of an amplifier 8a, while the two sectors 5a and 6b of the opposite electrode 5' are both connected to the output of the amplifier 8a.

In the whole, the two electrodes 5, 5' are connected to the feedback circuit of the amplifier 8a which, together with the resistance 8b, constitutes an integrating circuit known per se.

When a pulse P1 is sent to the aforesaid integrating circuit, the voltage is measured at the output of the amplifier 8a, which equals the dielectric permittivity of the fluid F between the two electrodes 5, 5'.

Since the positive terminal of the amplifier 8a is connected to physical ground, the electrode 5 connected to the negative terminal of the amplifier 8a is forced to the same ground potential, without however being physically connected to this ground.

As regards the measurement of the electrical conductivity, alternating voltage signals are preferably used which, advantageously, limit the measurement errors due transfer impedance in comparison with those that would occur if a direct voltage were used.

In fact, direct voltage signals would be blocked by capacitive component in the total transfer impedance, due to thin insulating layers of non-conductive media on the electrodes.

Preferably, the aforesaid variable voltage signals for measuring the electrical conductivity are comprised of a sinusoidal wave packet with frequency around 250 kHz.

Advantageously, the aforesaid frequency range was found to be a good compromise between the need to facilitate the measurement of the signal, which requires the use of low frequencies, and that of reducing the previously mentioned errors, which requires the use of high frequencies.

As regards the conductivity measurement circuit 10, and in particular its low impedance section A, it is preferable that it is configured to power the electrodes 5, 5' with reciprocally opposite voltages with respect to earth, for example in phase opposition.

Advantageously, this assures that all the current used for the measurement flows between the two electrodes and is therefore detectable, so as to guarantee the precision of the measurement.

In fact, if one of the electrodes were connected to earth, the voltage between the two electrodes would be lower than that of the power supply, due to the voltage drop induced by the resistance of the electronic switches even in closed state.

In this case, the other electrode would have a voltage toward earth greater than the voltage toward the other electrode and, therefore, an certain fraction of current would disperse toward earth, generating measurement errors.

Instead, the power supply as described above allows the creation of a preferential path for the current which remains confined between the two electrodes rather than dispersing to earth, to the benefit of the measurement precision.

The diagram shown in FIG. 5c presents an example of embodiment of that which has just been described.

The conductivity measure occurs by connecting the measurement circuit 10 to the electrodes 5, 5' by means of the respective switches 12.

A sinusoidal wave packet P2 is sent to the sectors 5b of the electrodes 5, 5' through corresponding amplifiers 10a and 10b, one of which reverses the phase of the current with respect to the input, so that the two electrodes 5, 5' are constantly in opposite phases.

At the same time, the differential amplifier V measures the voltage between the sectors 5a of electrodes 5, 5'.

The present invention also regards a method for measuring the properties of dielectric permittivity and electrical conductivity of a fluid F.

A method for measuring the properties of dielectric permittivity and electrical conductivity of a fluid F can be put into effect with any device 1 comprising two electrodes 4 and 4' facing each other from opposite sides of the containment volume 15 of the fluid F and able to be in electrical contact with the fluid, as schematically illustrated in FIG. 1.

Clearly, any one of the devices 1, 2 and 3 previously described, together with all their embodiments, are suited to be used in the aforesaid method.

The measurements of dielectric permittivity and electrical conductivity are carried out alternatingly by connecting the two distinct corresponding measurement circuits 8 and 9 to the two electrodes 4, 4'.

Therefore, advantageously, it is possible to measure both the dielectric permittivity and the electrical conductivity of the fluid F using a single pair of electrodes 4, 4', with the already mentioned advantages of reduced size and to costs.

Preferably, there is a first phase for identifying which of the two states, conductive or permittive, prevails in the fluid F, by means of a sequence of the two aforesaid measurements, performed alternatingly one after the other and repeated until identifying the state of the fluid.

The measurements can be carried out at any speed, although it is clear that, the larger the number of measurements per unit of time, the quicker the identification of the state of the fluid.

Preferably, the performance speed should be such as to allow two consecutive measurements of permittivity and conductivity to be carried out within an appreciably shorter time interval than that necessary for the fluid F to cover the length of the electrodes 4, 4'.

In this way, advantageously, the fluid field remains substantially unchanged during both measurements, therefore allowing the state of the fluid F to be identified almost instantaneously.

Preferably, once the conductive or permittive state of the fluid F has been identified, the method includes a second phase, in which only the electric quantity corresponding to said state of the fluid is measured, conductivity or permittivity, by keeping the corresponding measurement circuit connected to the electrodes.

The measurements of the aforesaid electric quantity are repeated until a change of state of the fluid F is detected.

In this case, the repetition is interrupted and a new repetition of the measurements of the electric quantity corresponding to the new state is started, by connecting the respective measurement circuit to the electrodes.

The new repetition will in turn be interrupted when a further change of state of the fluid F is detected.

According to the method of the invention, a measuring device of the type illustrated in FIG. 2 is used, which includes electrodes 5, 5' provided with at least two sectors 5a and 5b, each of which is suited to be in electrical contact with the fluid F separately from the other sector.

Preferably, in this case the method includes at least one measurement of the electrical conductivity between the electrodes 5, 5', carried out by injecting a current through two corresponding sectors 5a of the electrodes and, at the same time, measuring the voltage between the other sectors 5b, as illustrated to schematically in FIG. 5b.

The operation described above advantageously allows the electrical conductivity to be measured by means of the four-wire method previously described, to the benefit of measurement precision.

As regards the measurement of the dielectric permittivity, preferably this is performed with both sectors 5a and 5b of each electrode 5, 5' connected to each other, as illustrated in FIG. 5a, so that each electrode is used as a whole.

Clearly, instead of the electrode 5 of FIG. 2, the aforesaid method could be equally applied to a device including the embodiment 6 of FIG. 3, or any other embodiment having two separate sectors.

A further embodiment of the method of the invention uses the device 3 illustrated in FIG. 6a, in which a sector of each electrode 7, 7' includes at least two separate zones 7b and 7c of electrical contact with the fluid F.

Preferably, in this case, the method includes a third phase consisting of a sequence of measurements of only one electric quantity, dielectric permittivity or electrical conductivity, performed in sequence between each of the two corresponding pairs of zones 7b-7b and 7c-7c on the two electrodes 7, 7', as shown in FIG. 6c.

Advantageously, the aforesaid measurements can be processed by means of a cross-correlation algorithm known per se, in order to determine the speed of the fluid using a single measuring device 3.

In addition to the measurements described above, the third phase can also include a further measurement between the sectors 7a of the electrodes 7, 7'. In this way it is possible to make three different zones 7a, 7b and 7c available on each electrode 7, 7' and to perform as many measurements for the cross-correlation, to the benefit of measurement precision.

Given the above, it is understood that the device and the measuring method of the invention achieve all the set objects.

In particular, the device of the invention is more compact than the known devices with equivalent functionality, as it uses a single pair of electrodes to measure the dielectric permittivity of the fluid, its electrical conductivity and, in the case of the third embodiment described, also its speed.

In addition, the measurement of the conductivity and the permittivity is done by using a single pair of electrodes, so as to allow the execution of both measurements for the same zone of the fluid, with the advantage of ensuring a higher degree of precision compared to the known electrodes.

Similarly, the separation of each electrode in two sectors allows the attainment of greater measurement precision compared to the known devices, inasmuch as it enables the execution of the "four-wire method" measurement.

Upon implementation, the device and method of the invention can be subjected to further improvements or changes that, although not described herein and not represented in the drawings, must all be considered protected by the present patent, provided that they fall within the scope of the claims that follow.

Where technical features mentioned in any claim are followed by reference signs, those reference sings have been included for the sole purpose of increasing the intelligibility of the claims and accordingly such reference signs do not have any limiting effect on the protection of each element identified by way of example by such reference signs.

The invention claimed is:

1. Method for measuring the dielectric permittivity and the electrical conductivity of a fluid comprising the step of alternately connecting a first measurement circuit for measuring said dielectric permittivity and a distinct second measurement circuit for measuring said electrical conductivity to an electrode pair facing each other on opposite sides of a volume for containing said fluid, so as to be placed in electrical contact with said fluid, wherein each said electrode comprises at least two separate sectors, wherein each said sector is suited to establish an electrical contact with said fluid separately from the other sector, and wherein at least one of said electrical conductivity measurements includes the following steps, which are carried out simultaneously:
   injecting a current through first corresponding sectors of said electrodes;
   measuring the voltage between the other sectors of said electrodes; and
   determining said electrical conductivity as a function of the ratio between said injected current and said measured voltage
       wherein, when said electrodes are connected to said dielectric permittivity measurement circuit, the sectors of each electrode are connected to one another
       wherein a sector of each one of said electrodes comprises at least two separate zones in electrical contact with said fluid, said method comprising at least a first measurement phase including a sequence of measurements of the same electric property chosen between permittivity and conductivity, wherein said sequence comprises a measurement between a first pair of corresponding zones on the two electrodes and at least a subsequent measurement between a second pair of said corresponding zones.

2. Method according to claim 1, wherein it comprises a second measurement phase including a sequence of dielectric permittivity measurements alternating with electrical conductivity measurements, repeated unto the identification of a predominantly conductive or predominantly permittive state of said fluid is achieved.

3. Method according to claim 2, wherein it comprises a third measurement phase including a sequence of measurements of only the electric property corresponding to the state of the fluid identified in said second phase.

4. Method according to claim 3, wherein, when said measurements indicate that said fluid has switched to the other state, said third phase is interrupted and is repeated by measuring the electric property corresponding to the new state.

* * * * *